United States Patent
Rockwood, Jr.

(10) Patent No.: US 6,558,425 B2
(45) Date of Patent: *May 6, 2003

(54) SHOULDER PROSTHESIS WITH HUMERAL FRACTURE STEM

(75) Inventor: Charles A. Rockwood, Jr., San Antonio, TX (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/892,687

(22) Filed: Jun. 27, 2001

(65) Prior Publication Data

US 2001/0037152 A1 Nov. 1, 2001

Related U.S. Application Data (63) Continuation of application No. 09/483,749, filed on Jan. 17, 2000, now Pat. No. 6,283,999, which is a continuation-in-part of application No. 09/394,557, filed on Sep. 10, 1999, now Pat. No. 6,277,123.
(60) Provisional application No. 60/123,860, filed on Mar. 12, 1999, and provisional application No. 60/117,984, filed on Jan. 29, 1999.

(51) Int. Cl.⁷ .................................................. A61F 2/40
(52) U.S. Cl. .................................................. 623/19.12
(58) Field of Search .......................... 623/19.11–19.14, 623/22.11, 23.26

(56) References Cited

U.S. PATENT DOCUMENTS

| | | | |
|---|---|---|---|
| 4,045,825 A | | 9/1977 | Stroot |
| 4,919,670 A | * | 4/1990 | Dale et al. .................... 623/19 |
| 5,314,479 A | * | 5/1994 | Rockwood, Jr. et al. ....... 623/19 |
| 5,358,526 A | | 10/1994 | Tornier |
| 5,507,817 A | | 4/1996 | Craig et al. |
| 5,658,340 A | | 8/1997 | Muller et al. |
| 5,728,161 A | | 3/1998 | Camino et al. |
| 5,910,171 A | | 6/1999 | Kummer et al. |
| 5,944,758 A | | 8/1999 | Mansat et al. |
| 5,961,555 A | | 10/1999 | Huebner |
| 6,033,439 A | * | 3/2000 | Camino et al. ................ 623/19 |

(List continued on next page.)

FOREIGN PATENT DOCUMENTS

| | | | | |
|---|---|---|---|---|
| JP | 2001095826 A | * | 4/2001 | ............. A61F/2/40 |
| WO | WO 96/17553 | | 6/1996 | |
| WO | WO 98/15241 | | 4/1998 | |

OTHER PUBLICATIONS

Biomet Bi–Angular brochure (one page), published at least as early at Jan. 29, 1999.
Biomet Bio–Modular/Bi–Polar Shoulder Arthoplasty brochure (two pages), BioMet, Inc., copyright 1997.

(List continued on next page.)

*Primary Examiner*—Eduardo C. Robert
*Assistant Examiner*—Michael B. Priddy
(74) *Attorney, Agent, or Firm*—Maginot, Moore & Bowman (57) ABSTRACT

A shoulder prosthesis including a fracture stem has body having an exterior surface, a shank attached to the body and a head. The body includes a medial fin, an anterior fin and a posterior fin. The medial fin includes a suture hole. The anterior and posterior fins each include a plurality of suture holes. The prosthesis further includes a lateral suture hole intersecting the exterior surface of the body. The lateral suture hole may be formed in a projection on the lateral side of the prosthesis. In an alternative embodiment, a trail prosthesis includes indicia for noting the proper placement of the stem. The prosthesis includes corresponding indicia for replicating the placement of the trial stem.

20 Claims, 5 Drawing Sheets

U.S. PATENT DOCUMENTS

| | | | |
|---|---|---|---|
| 6,045,582 | A | 4/2000 | Prybyla |
| 6,102,953 | A | 8/2000 | Huebner |
| 6,120,542 | A | 9/2000 | Camino et al. |
| 6,129,764 | A | 10/2000 | Servidio |
| 6,168,627 | B1 | 1/2001 | Huebner |
| 6,168,628 | B1 | 1/2001 | Huebner |
| 6,171,341 | B1 | 1/2001 | Boileau et al. |
| 6,193,758 | B1 * | 2/2001 | Huebner .................. 623/19.14 |
| 6,197,063 | B1 * | 3/2001 | Dews ...................... 623/19.14 |
| 6,283,999 | B1 * | 9/2001 | Rockwood, Jr. ......... 623/19.12 |

OTHER PUBLICATIONS

The Kirschner Integrated Shoulder System brochure (three pages), Kirschner Medical Corporation, published as early as Jan. 29, 1999.

Cofield2 Total Shoulder System brochure (one page), Smith & Nephew Richards, Inc., published at least as early as Jan. 29, 1999.

Cofield Total Shoulder System brochure (six pages), Smith & Nephew Richards, Inc., published at least as early as Jan. 29, 1999.

Intermedics Orthopedics Select Shoulder System brochure (two pages), Intermedics Orthopedics, Inc., copyright 1993.

Fenlin Total Shoulder System brochure (one page), published at least as early as Jan. 29, 1999.

Foundation Total Shoulder System (three pages), Encore Orthopedics, Inc., copyright 1996.

Aequalis Surgical Technique Shoulder Prosthesis (two pages), Tornier, Inc., published at least as early as Jan. 29, 1999.

Osteonics Shoulder System brochure (seven pages), published at least as early as Jan. 29, 1999.

Total Shoulder Products publication by DePuy dated Apr. 24, 1998.

Single page publication from Conference Booklet with "Convention Center Room 90–92" caption at top of page and dated Monday, Mar. 23, 1998.

* cited by examiner

SHOULDER PROSTHESIS WITH HUMERAL FRACTURE STEM

This application is a continuation of application Ser. No. 09/483,749, filed on Jan. 17, 2000, now U.S. Pat. No. 6,283,999 which in turn is a continuation-in-part of application Ser. No. 09/394,557, filed on Sep. 10, 1999, now U.S. Pat. No. 6,277,123 which in turn claims the benefit of both U.S. Provisional Application Ser. No. 60/123,860, filed on Mar. 12, 1999 and U.S. Provisional Application Ser. No. 60/117,984, filed on Jan. 29, 1999.

BACKGROUND AND SUMMARY OF THE INVENTION

The present invention relates to a prosthesis, and, in particular, to a shoulder prosthesis including a humeral stem. The present invention also relates to a method for determining a desirable humeral stem height.

Figure 1:
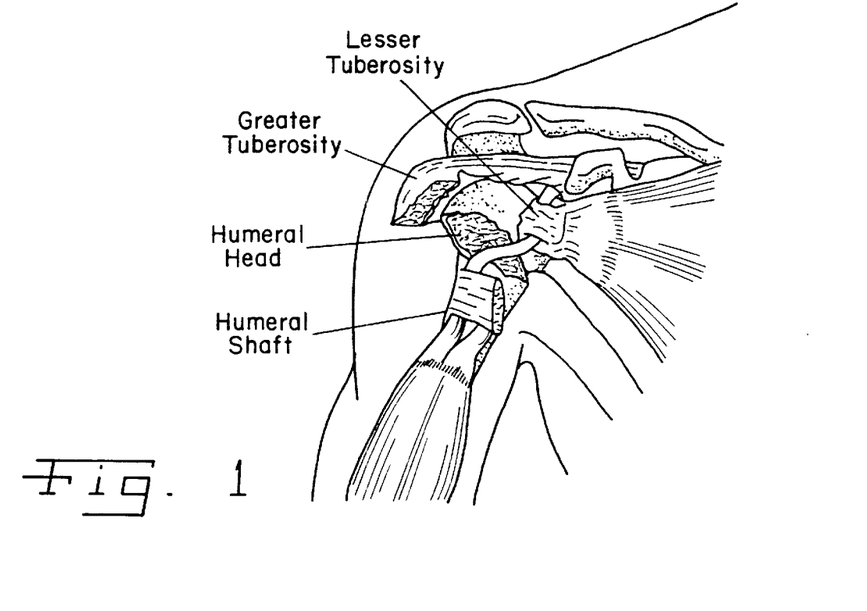
FIG. 1 is a view of a four part proximal humeral fracture.

Various artificial shoulder prostheses with humeral stems are known. Two examples of such prosthesis are shown in U.S. Pat. Nos. 5,728,161 and 5,314,479. The prosthesis of the '161 patent generally includes a shank portion, a head portion and an attachment mechanism for securing the head portion to the shank portion. Some prosthetic shoulders, such as that shown in FIG. 1 of the '161 patent, include one or more fins formed on the body portion of the device. The fins may include suture holes. In other prosthetic shoulders, some or all of the fins do not include suture holes. Such a device is shown in FIG. 1 of the '479 patent. Additional shoulder prosthesis are shown and discussed in U.S. Pat. No. 5,032,132 to Matsen et al.; U.S. Pat. No. 4,865,605 to Dines et al.; U.S. Pat. No. 4,919,670 to Dale et al.; U.S. Pat. No. 5,358,526 to Tornier, U.S. Pat. No. 5,507,817 to Craig et al.; U.S. Pat. No. 4,045,825 to Stroot; and U.S. Pat. No. 4,042,980 to Swanson et al.

Shoulder prostheses are sometimes used to repair what is known as a "four part humeral fracture." Such a fracture typically occurs in the proximal region of the humerus. Often, the humeral head, greater tubercle and lesser tubercle separate from the humeral shaft, thus leaving four parts. A shoulder prosthesis may be used to replace the humeral head and provide a point of attachment for the greater and lesser tubercles.

One embodiment of the present invention provides a shoulder prosthesis including a body having an exterior surface, a shank connected to the body, a head connected to the body, a medial fin connected to the body, the medial fin including at least one suture hole, a posterior fin connected to the body, the posterior fin including at least one suture hole, an anterior fin connected to the body, the anterior fin including at least one suture hole and at least one lateral suture hole intersecting the exterior surface of the body. The suture hole may be formed in a projection on the exterior surface of the body. At least one of the anterior and posterior fins may extend farther above the exterior surface of the body than the projection. At least one of the anterior and posterior fins may extend at least twice as far above the exterior surface of the body as the projection. A plurality of the suture holes in the anterior and posterior fins and the lateral suture hole may lie in the same plane.

According to another embodiment of the present invention, a shoulder prosthesis includes a body having an exterior surface, a shank connected to the body, a first suture hole located on the lateral side of the prosthesis and an anterior fin connected to the exterior surface of the body, the anterior fin having a second suture hole the center of which is spaced farther from the exterior surface of the body than the center of the first suture hole. The first suture hole may intersect the exterior surface of the body and may be formed in a projection on the exterior surface of the body. In one embodiment, the anterior fin extends farther above the exterior surface of the body than the projection. The anterior fin may extend at least twice as far above the exterior surface of the body as the projection. The shoulder prosthesis may include a posterior fin having a third suture hole the center of which is spaced farther from the exterior surface of the body than the center of the first suture hole. The first, second and third suture holes may lie in the same plane.

According to another embodiment of the present invention, a shoulder prosthesis includes a body having an exterior surface, a shank portion attached to the body, the shank portion configured to be received within the medullary canal of a human humerus, an anterior fin including at least one suture hole, the anterior fin and at least one suture hole providing an attachment point for the greater and lesser tubercles and a least one lateral suture hole intersecting the exterior surface of the body, the at least one lateral suture hole providing an attachment point for the greater tubercle to prevent rotation of the greater tubercle. At least one lateral suture hole may be formed in a projection on the exterior surface of the body. The anterior fin may extend farther above the exterior surface of the body than the projection and may extend at least twice as far above the exterior surface of the body as the projection. The prosthesis may also include a posterior fin including at least one suture hole, the posterior fin and at least one suture hole providing an attachment point for the greater and lesser tubercles. In one embodiment, at least one lateral suture hole lies in the same plane as at least one of the suture holes in the anterior fin and at least one of the suture holes in the posterior fin.

According to an additional embodiment, a trial stem is provided with measurement indicia thereon and a shoulder prosthesis is provided with corresponding indicia thereon.

Also according to the present invention, a method is provided for positioning a shoulder prosthesis so as to allow for ample space for anatomic reconstruction of the tuberosities and anatomic reconstruction of the humeral articular surface. The method includes using a trial prosthesis, noting the position an indicia on the trial and upon implantation of the actual prosthesis, positioning a corresponding indicia in the same location.

Other features of the present invention will be apparent to those of ordinary skill in the art from the following detailed description of the preferred embodiments and accompanying drawings.

DETAILED DESCRIPTION OF THE DRAWINGS

FIG. 1 illustrates a typical four part humeral fracture. In such a fracture, the humeral head breaks free and does not have any soft tissue attachment or blood supply. The greater tuberosity is displaced superiorly and posteriorly by the pull of the attached rotator cuff while the lesser tuberosity is retracted medially by the pull of the subscapularis. The neck of the humeral shaft is displaced medially by the pull of the pectoralis major. Other variations of the four part humeral fracture are also possible. The shoulder prostheses of the present invention are useful for repairing the fracture shown in FIG. 1, including other variations, and for correcting other deformities and injuries to the shoulder joint and humerus.

Figure 2:
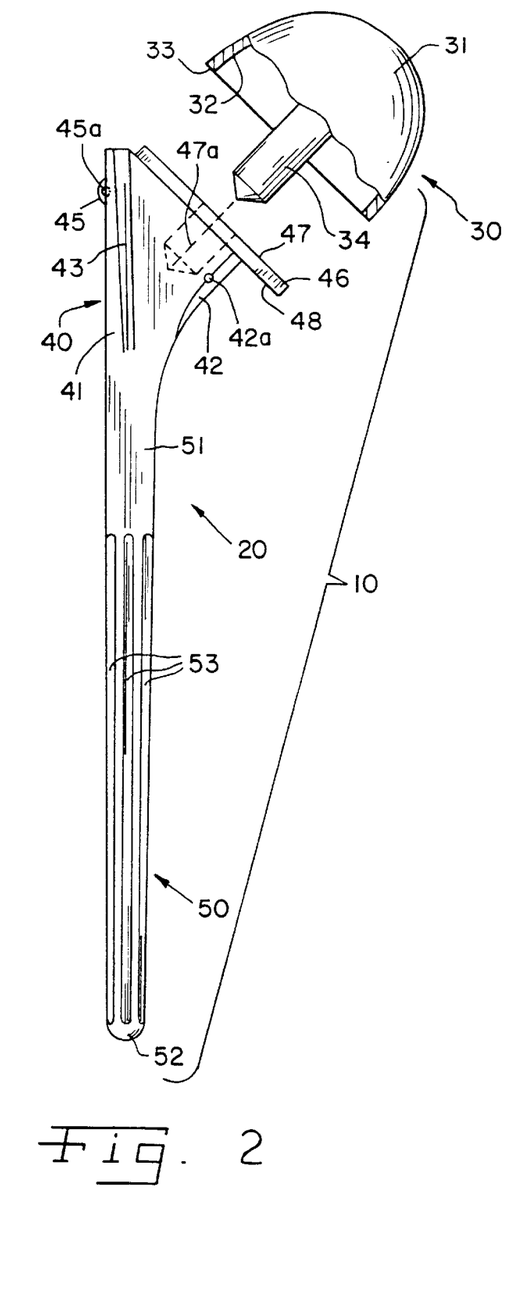
FIG. 2 is an exploded side elevational view of one embodiment of a shoulder prosthesis according to the present invention.

FIG. 2 is a side elevational view of a shoulder prosthesis 10 according to one embodiment of the present invention. Prosthesis 10 generally includes a stem portion 20 and a head portion 30. Stem portion 20 generally includes a body portion 40 and a shank portion 50.

Body portion 40 includes an exterior surface 41 having a first or medial fin 42, a second fin 43, and a third fin 44 connected thereto. Note that depending on the arm into which prosthesis 10 is inserted, fins 43 and 44 are either the anterior or posterior fin. For example, if the view of FIG. 2 is considered a posterior view, the prosthesis would be in the patient's left arm and fin 43 would be a posterior fin, while fin 44 would be an anterior fin. Conversely, if the view shown in FIG. 2 is considered an anterior view, the prosthesis would be located in the patient's right arm, thereby making fin 43 the anterior fin and fin 44 the posterior fin.

Fin 42 includes a suture hole 42a which partially intersects exterior surface 41 of body portion 40. Fin 43 includes a first or proximal suture hole 43a, a second or middle suture hole 43b, and a third or distal suture hole 43c. Similarly, fin 44 has a first or proximal suture hole 44a, a second or middle suture hole 44b, and a third or distal suture hole 44c. Body portion 40 further includes a lateral projection 45. Note that in the embodiment shown, fins 43 and 44 both extend farther above exterior surface 41 than does projection 45. In fact, in the embodiment shown, fins 43 and 44 both extend at least twice as far above exterior surface 41 than does projection 45.

A lateral suture hole 45a is formed partially within lateral projection 45 and partially within body portion 40. That is, suture hole 45a intersects or cuts into exterior surface 41 of body portion 40. This is in contrast to the suture holes in fins 43 and 44, which do not, in the embodiment shown, intersect exterior surface 41 of body portion 40. Rather, they are entirely located within fins 43 and 44. Additionally, in the embodiment shown, the center of each of suture holes 43a, 43b, 43c, 44a, 44b and 44c are all spaced farther from exterior surface 41 of body 40 than the center of suture hole 45a.

Figure 3:
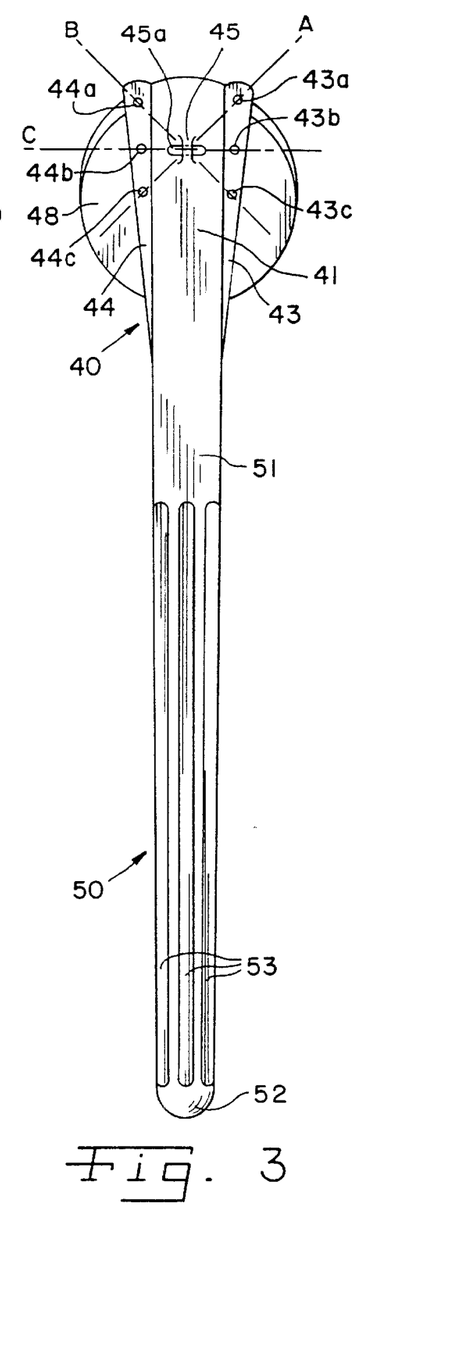
FIG. 3 is a lateral elevational view of the shoulder prosthesis shown in FIG. 2.
Figure 4:
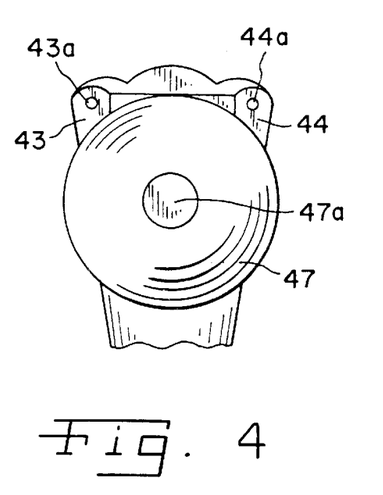
FIG. 4 is a plan view of the collar of the shoulder prosthesis shown in FIG. 2.

In the embodiment shown, suture holes 43a, 45a and 44c are located in a common plane indicated by the letter "A" in FIG. 3. Similarly, in the embodiment shown, suture holes 44a, 45a and 43c lie in a common plane indicated by the letter "B" in FIG. 4. Likewise, suture holes 43b, 45a and 44b lie in a common plane indicated by the letter "C" in FIG. 4.

Body portion 40, in the embodiment shown, further includes a collar 46. Collar 46 includes a first or proximal surface 47 and a second or distal surface 48. An opening 47a extends through collar 46 and into body portion 40. Opening 47a is used to secure head 30 to stem portion as described below. In the embodiment shown, collar 46 is generally circular and integrally formed with body portion 40. However, collar 46 could be formed as a separate piece and attached to body 40 in any of a number of ways. One such way is shown in U.S. Pat. No. 5,314,479, the disclosure of which is hereby incorporated by reference.

Shank portion 50 includes a first or proximal end 51 adjacent body portion 40 and a second or distal end 52. Shank portion 50 may be formed as a unitary piece with body portion 40. Alternatively, shank portion 50 may be formed in one or more pieces and attached to body portion 40 in any one of a number of known manners. One example of such a means or apparatus for attaching a shank portion to a body portion of a shoulder prosthesis is shown in U.S. Pat. No. 5,314,479, the disclosure of which is incorporated herein by reference. Shank portion 50 tapers such that it is narrower near distal end 52 and wider at proximal end 51. This taper of the stem helps to properly load the cement mantle when the prosthesis is inserted, thereby properly transferring forces from the implant to the humeral shaft. In the embodiment shown, the stem portion 50 also includes a plurality of flutes 53. Flutes 53 improve the adhesion of the bone cement to the shank. Flutes 53 also improve the rotational stability of the device when implanted.

Head 30 is designed to replace the humeral head and articulate within the glenoid cavity as is well known in the art. Head 30 generally includes a first or articulating surface 31, a second interior surface 32, a third or distal surface 33, and an attachment post or projection 34. Projection 34 and the interior of head 30 are configured such that projection 34 will be received within opening 47a and collar 46 will be located on the interior of head 30 such that surface 33 contacts body portion 40 on the lateral side of the prosthesis. Projection 34 and opening 47a are, in the embodiment shown, configured in the form of a taper lock or Morse taper, as is known in the art. Alternative methods of attaching head 30 to body potion 40 could also be used, such as those disclosed in U.S. Pat. No. 5,314,479.

Figure 5:
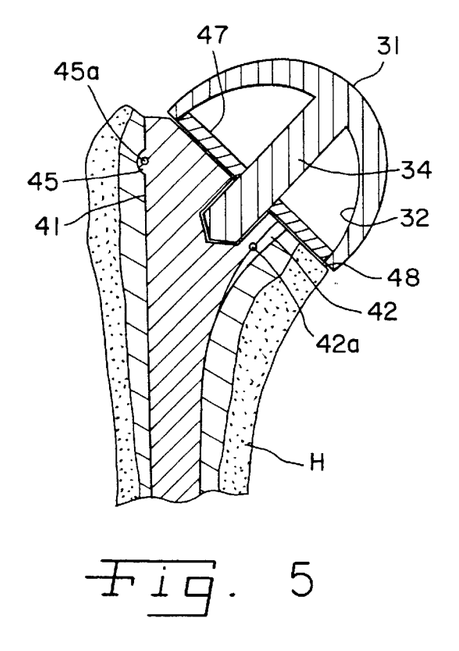
FIG. 5 is a side elevational view of the shoulder prosthesis shown in FIG. 2 implanted in a patient's arm.

FIG. 5 shows a cross-sectional view of the prosthesis of FIG. 1 implanted in a human humerus. To implant the prosthesis of the present invention in, for example, a humerus that has suffered a four part humeral fracture, the intramedullary canal is reamed to the appropriate size and configuration for the device to be implanted. Bone cement is then introduced into the prepared cavity, as is known in the art, and distal end 52 is inserted into the cavity. Shank 50 is pushed further into the cavity until the desired insertion depth is reached.

As noted above, a plurality of suture holes 42a, 43a, 43b, 43c, 44a, 44b, 44c and 45a are provided on body portion 40. Suture holes 43a, 43b and 43c in fin 43 and 44a, 44b and 44c in fin 44 may be utilized to reattach the lesser tubercle. The fin to which the lesser tubercle is attached will depend on the arm into which the prosthesis is implanted. To reattach the lesser tubercle, a groove corresponding to the shape of fin 43 or 44 is formed in the lesser tubercle and one or more sutures are tied to the lesser tubercle through one or more of suture holes 43a, 43b and 43c or 44a, 44b and 44c, depending on whether the lesser tubercle is attached to fin 43 or 44.

In the typical four part humeral fracture, it is also necessary to reattach the greater tubercle. It has been found in many four-part humeral fractures that better positioning of greater tubercle can be obtained if it is attached to the anterior and/or posterior fins. However, in some prior art devices, the body portion includes a projecting lateral fin with one or more suture holes. In such devices, the suture holes are sometimes placed too far from the surface of the body for proper attachment of the greater tubercle. Thus, the device may provide an anatomically improper attachment location for the greater tubercle. Note also that in such devices it would be necessary to cut a groove in the surface of the greater tubercle to provide space for the lateral fin.

Some prior art devices do not include any lateral suture holes. Thus, the greater tubercle cannot be improperly attached at a lateral location. However, it has also been found that in some instances it may be desirable to provide a point of lateral attachment for the greater tubercle to prevent anterior rotation of the greater tubercle from the pull of the attached muscles. The present invention provides a single lateral suture hole 45a for this purpose. Note that the lateral suture hole is positioned closely adjacent the body portion 40 and, in the embodiment shown, actually intersects outer surface 41 of body portion 40. This provides a more anatomically correct attachment point for the greater tubercle than a prosthesis in which the suture holes are spaced further from the body portion of the prosthesis. Note also that the elimination of the lateral fin in the embodiment shown means that it is not necessary to cut a groove in the greater tubercle. Instead, it may only be necessary to make a small indentation to accommodate projection 45.

Thus, in the present invention, the greater tubercle is attached to either or both of fins 43 and 44 by sutures that extend through one or more of suture holes 43a, 43b, 43c, 44a, 44b and 44c. If necessary, the greater tubercle may also be secured by a suture extending through suture hole 45a.

When the prosthesis is fully inserted and the greater and lesser tubercles are reattached, distal surface 48 of collar 46 will rest on the tubercles. Note that this placement of collar 46 will help to transmit loads on the shoulder to the humeral bone. Head 30 is then attached to body 40 by inserting projection 34 into opening 47a and impacting the head to engage the Morse taper.

FIGS. 6–11 show an alternative embodiment of the present invention. When implanting a shoulder prosthesis, it is necessary to determine the desirable rotational position and height of the stem portion in the humerus. Accordingly, a trial stem and shoulder prosthesis including indicia to allow a surgeon to transfer the already determined height requirements from the trial to the prosthesis are provided.

Figure 6:
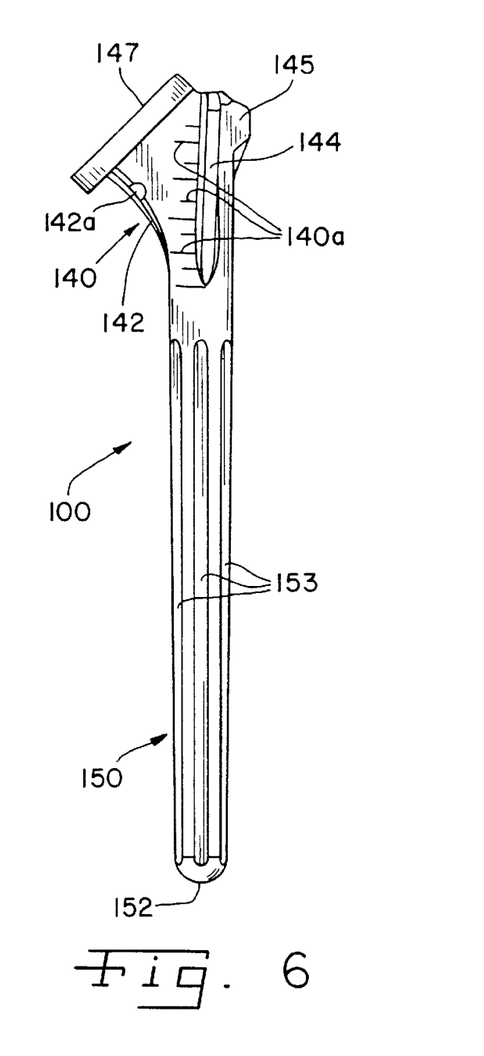
FIG. 6 is a side elevational view of a trial stem having indicia starting at an inferior aspect of anterior and posterior fins and extending spaced-apart from one another, alternating with short and long lines.
Figure 7:
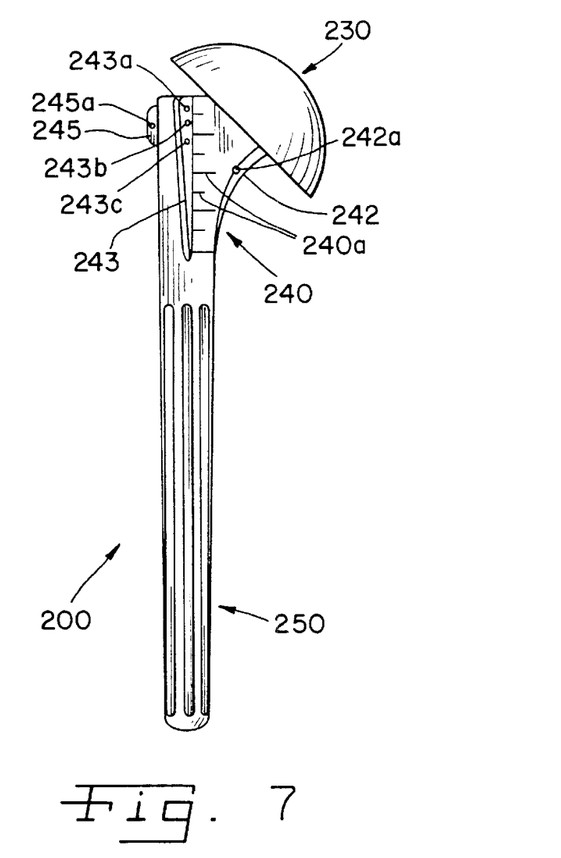
FIG. 7 is a side elevational view of a shoulder prosthesis according to another embodiment of the present invention including indicia spaced apart from one another to mark the appropriate position of the prosthesis in relation to the humeral shaft, and an anterior fin.

FIG. 6 illustrates a trial stem according to one embodiment of the present invention. Trial stem 100 generally includes the same parts and features as stem portion 20 of shoulder prosthesis 10. Accordingly, in FIG. 6, elements of trial stem 100 corresponding to elements of stem portion 20 are indicated by the same number with the addition of the numeral "1" at the beginning. Body portion 140 of trial stem 100 includes a plurality of indicia 140a. Indicia 140a may be placed on one or both sides of body portion 140. Alternatively, indicia 140a may be placed at any location where they will be sufficiently visible so as to allow the surgeon to determine the proper placement of the prosthesis. Indicia 140a may be placed on body portion 140 in any one of a number of manners. For example, indicia 140a may be etched or engraved on body portion 140. Alternatively, indicia 140a may be marked on body portion 140 with an appropriate ink, paint or similar substance. Indicia 140a could be coupled to body portion 140 using adhesive, fasteners or any other suitable means. Holes or similar features can also be used as indicia 140a. Indicia 140a may be spaced apart in any desired pre-determined units, such as inches or centimeters. Indicia 140a could also be color coded or marked in any other manner suitable to indicate to a user various measurements. Preferably, the indicia 140a are lines spaced-apart about 5 mm. It is appreciated that this spacing could be either more or less. Indicia 140a may be marked with numbers. For example, the distal most line could be numeral 0, then numeral 5 for the next line, etc. The height of stem portion 120 may also be gauged by an additional series of holes, dimples or other markings in or on fins 143 and/or 144, or holes or dimples in body portion 140.

FIGS. 7–11 illustrate an alternative embodiment of a shoulder prosthesis according to the present invention. Shoulder prosthesis 200 generally includes the same parts and features as shoulder prosthesis 10. Accordingly, in FIGS. 7–11, elements of shoulder prosthesis 200 corresponding to elements of shoulder prosthesis 10 are indicated by the same number with the addition of the numeral "2" at the beginning. Body portion 240 of stem portion 220 includes indicia 240a corresponding to indicia 140a on body portion 140 of stem portion 120. Indicia 240a may be formed and positioned in any of the manners discussed above with respect to indicia 140a.

Figures 8, 9:
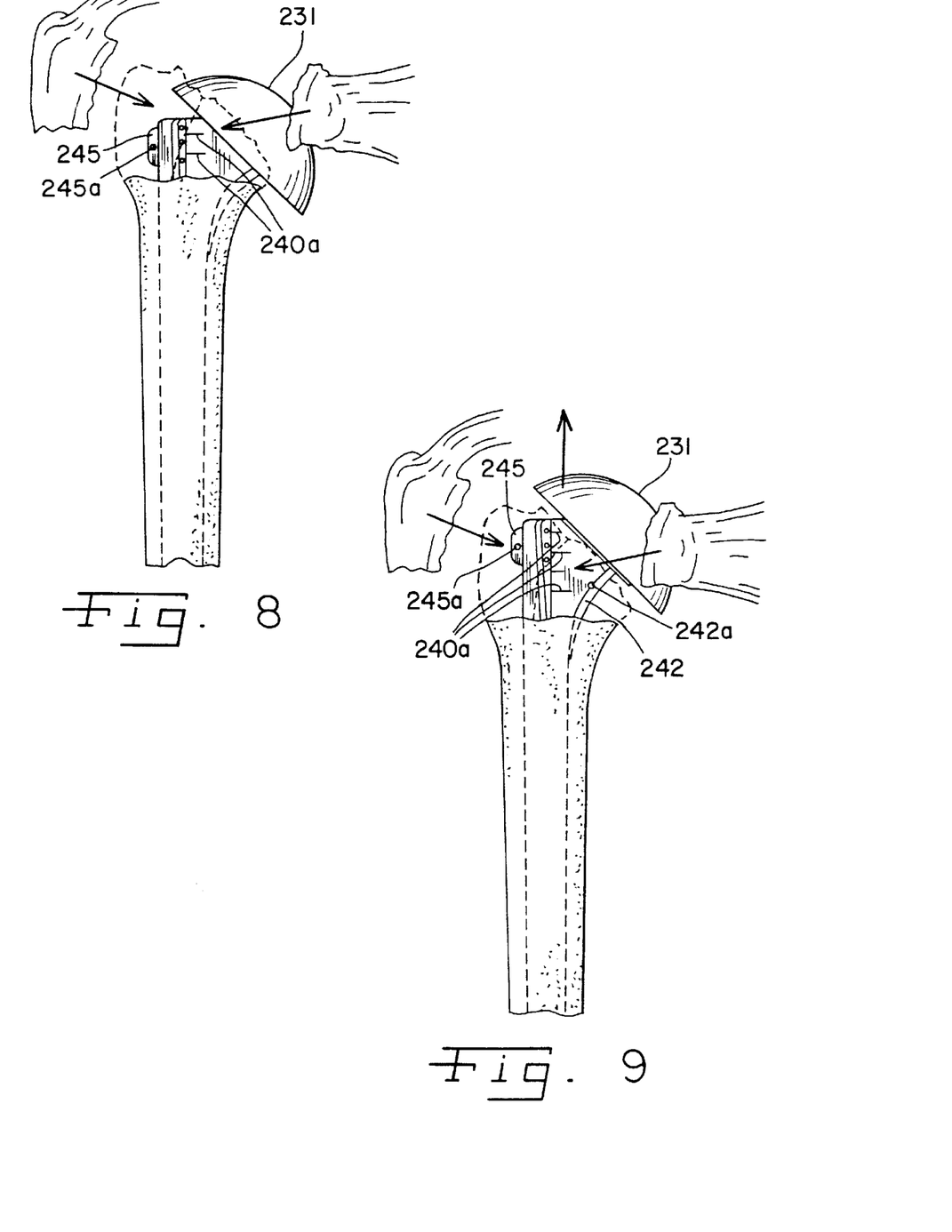
FIGS. 8–10 are views of the prosthesis of FIG. 7 being positioned in various locations.
Figure 10:
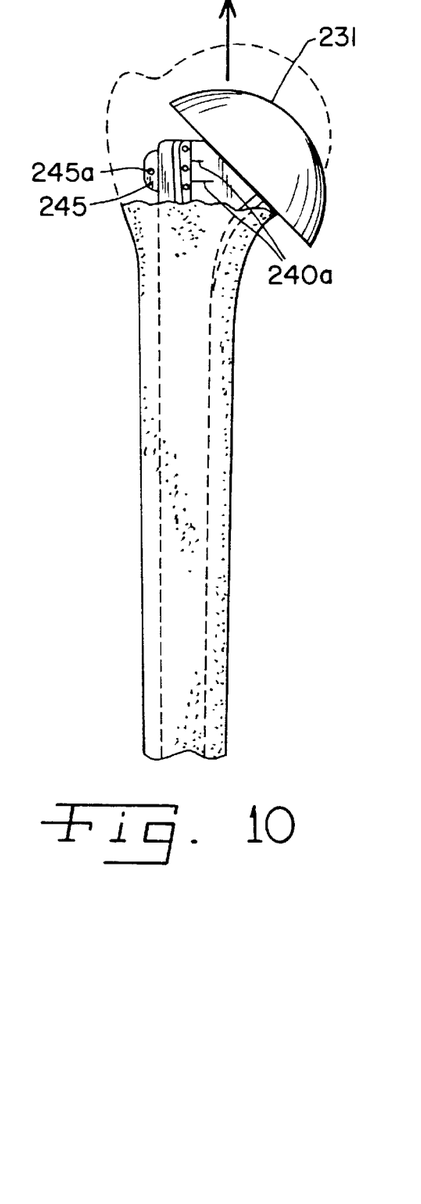
Figure 11:
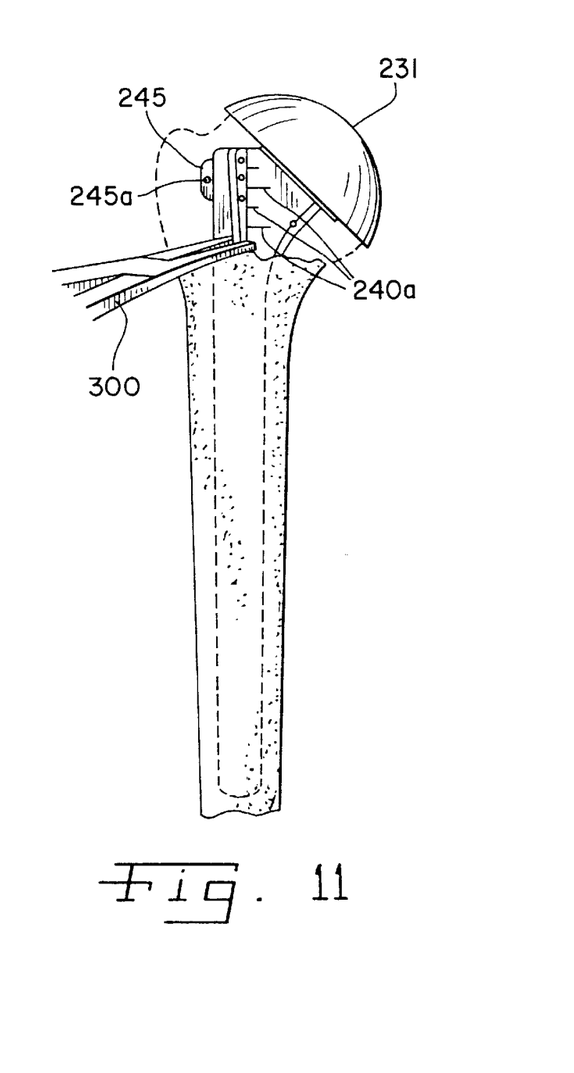
FIG. 11 is a view of the prosthesis of FIG. 7 positioned to preserve space for anatomic reconstruction of the tuberosities.

In use, stem portion 120 of trial 100 is placed into the prepared intramedullary canal of the humerus and rotated and raised or lowered until there is sufficient space for the tuberosity reconstruction and sufficient joint range of motion. The joint range of motion can be evaluated by assembling a trial humeral head to stem portion 120 and preforming a trial reduction, as is well known in the art. Once the desired position of stem portion 120 is determined, it can be gauged or measured by noting the position of a given indicia 140a. The surgeon then removes stem portion 120. After removing stem portion 120, The surgeon inserts stem portion 220 of prosthesis 200 into the prepared intramedullary canal of the humerus until the indicia 240a corresponding to the noted indicia 140a is properly positioned. FIGS. 8–11 illustrate positioning of prosthesis 200 in the humerus. For example, prosthesis 200 is shown in FIG. 9 as having been raised from the position shown in FIG. 8. According, additional indicia 240a are visible. FIGS. 10 and 11 illustrate this in another manner. FIG. 10 shows the desired position of the humeral articular surface for head 230 in dashed lines. FIG. 11 shows the prosthesis 200 raised such that head 230 is in the proper position and being held in place by a surgical instrument 300.

Although the present invention has been shown and described in detail, the same is for purposes of illustration only and is not intended to limit the scope of the invention. Numerous changes may be made to the embodiments discussed without departing from the scope and spirit of the present invention. For example, a plurality of stems, bodies, collars and heads could be provided to produce a prosthetic kit in which the pieces can be interchanged to customize the prosthesis. Additionally, the various components can take shapes other than those specifically illustrated in the embodiments discussed. Stem portion 50 could also be provided with a porous coating or other bone in growth material to enhance fixation. Furthermore, use of the device is not limited to four part humeral fractures. Accordingly, the scope of the present invention is to be limited only by the terms of the attached claims.

What is claimed is:

1. A shoulder prosthesis, comprising:
   a body having an exterior surface;
   a shank connected to said body;
   a head connected to said body; and
   a lateral projection extending from said body, wherein said lateral projection has a lateral suture hole defined therein which intersects an exterior surface of said body.

2. The shoulder prosthesis of claim 1, further comprising a medial fin connected to said body and defining at least one medial suture hole.

3. The shoulder prosthesis of claim 1, further comprising a posterior fin connected to said body and defining at least one posterior suture hole.

4. The shoulder prosthesis of claim 1, further comprising an anterior fin connected to said body and defining at least one anterior suture hole.

5. The shoulder prosthesis of claim 1, further comprising at least one indicia on said body for assisting in positioning of the prosthesis.

6. The shoulder prosthesis of claim 3, wherein said posterior fin extends farther above said exterior surface of said body than said projection.

7. The shoulder prosthesis of claim 4, wherein said anterior fin extends farther above said exterior surface of said body than said projection.

8. The shoulder prosthesis of claim 6, wherein said posterior fin extends at least twice as far above said exterior surface of said body as said projection.

9. The shoulder prosthesis of claim 7, wherein said anterior fin extends at least twice as far above said exterior surface of said body as said projection.

10. The shoulder prosthesis of claim 3, wherein said posterior fin includes a distal posterior suture hole, a middle posterior suture hole, and a proximal posterior suture hole.

11. The shoulder prosthesis of claim 4, wherein said anterior fin includes a distal anterior suture hole, a middle anterior suture hole, and a proximal anterior suture hole.

12. A shoulder prosthesis, comprising:
    a body having an exterior surface;
    a shank portion attached to said body and configured to be received within the medullary canal of a humerus bone;
    a lateral projection extending from said body, wherein said lateral projection has a lateral suture hole defined therein which intersects an exterior surface of said body.

13. The shoulder prosthesis of claim 12, further comprising a medial fin connected to said body and defining at least one medial suture hole.

14. The shoulder prosthesis of claim 12, further comprising a posterior fin connected to said body and defining at least one posterior suture hole.

15. The shoulder prosthesis of claim 12, further comprising an anterior fin connected to said body and defining at least one anterior suture hole.

16. The shoulder prosthesis of claim 12, further comprising at least one indicia on said body for assisting in positioning of the prosthesis.

17. The shoulder prosthesis of claim 14, wherein said posterior fin extends farther above said exterior surface of said body than said projection.

18. The shoulder prosthesis of claim 15, wherein said anterior fin extends farther above said exterior surface of said body than said projection.

19. The shoulder prosthesis of claim 17, wherein said posterior fin extends at least twice as far above said exterior surface of said body as said projection.

20. The shoulder prosthesis of claim 18, wherein said anterior fin extends at least twice as far above said exterior surface of said body as said projection.

* * * * *